United States Patent [19]

Holm et al.

[11] 4,238,219

[45] Dec. 9, 1980

[54] INCREASING CHLOROETHYLPHOSPHONIC ACID-INDUCED ETHYLENE RESPONSE

[75] Inventors: Robert E. Holm; Han San Ku, both of Painesville, Ohio

[73] Assignee: Diamond Shamrock Corporation, Dallas, Tex.

[21] Appl. No.: 879,963

[22] Filed: Feb. 21, 1978

Related U.S. Application Data

[63] Continuation of Ser. No. 722,805, Sep. 13, 1976, abandoned, which is a continuation-in-part of Ser. No. 610,916, Sep. 8, 1975, abandoned.

[51] Int. Cl.$^3$ ............................................. A01N 57/12
[52] U.S. Cl. ........................................... 71/86; 71/90; 71/92; 71/95; 71/97; 71/105
[58] Field of Search .............................................. 71/86

[56] References Cited

U.S. PATENT DOCUMENTS 3,879,188   4/1975   Fritz et al. ................................ 71/86

Primary Examiner—Catherine L. Mills
Attorney, Agent, or Firm—Stuart L. Melton

[57] ABSTRACT

A composition consisting essentially of 2-chloroethylphosphonic acid and certain imides, carbamates, or tetrachloroisophthalonitrile, increases the ability of 2-chloroethylphosphonic acid alone to cause the release of ethylene in plant tissue when applied to same.

5 Claims, No Drawings

INCREASING CHLOROETHYLPHOSPHONIC ACID-INDUCED ETHYLENE RESPONSE

CROSS REFERENCE TO RELATED APPLICATIONS

This application is a continuation of copending application Ser. No. 722,805, filed Sept. 13, 1976, now abandoned which, in turn, is a continuation-in-part of copending application Ser. No. 610,916, filed Sept. 8, 1975, now abandoned.

BACKGROUND OF THE INVENTION

The release of ethylene within plant tissue is by now known to effect a wide variety of responses, such as increased ripening, fruit abscission, increased growth rate, yield, etc.

One compound known to be capable of causing the release of ethylene in a wide variety of plants is 2-chloroethylphosphonic acid. See U.S. Pat. No. 3,879,188. The compound is, however, both expensive and phytotoxic when used at the elevated concentrations sometimes needed.

STATEMENT OF THE INVENTION

Therefore, it is an object of the present invention to provide a composition and method for increasing the ability of 2-chloroethylphosphonic acid to cause the release of ethylene in plant tissue.

This and other objects of the present invention will become apparent to those skilled in the art from the specification and claims that follow.

There has now been found a composition consisting essentially of 2-chloroethylphosphonic acid and a compound from the group N-[(trichloromethyl)thio]phthalimide, cis-N-[(trichloromethyl)thio]-4-cyclohexene-1,2-dicarboximide, cis-N-[(1,1,2,2-tetrachloromethyl)thio]-4-cyclohexene-1,2-dicarboximide, ferric dimethyldithiocarbamate, ethylenebisdithiocarbamate manganese, ethylenebisdithiocarbamate zinc, methyl-1-(butylcarbamoyl)-2-benzimidazolecarbamate, or tetrachloroisophthalonitrile. When a plant is contacted with a growth regulating amount of said composition, the ability of the 2-chloroethylphosphonic acid to release ethylene in the plant tissue is increased. This ethylene release may be attributable to both chloroethylphosphonic acid degradation and the attendant triggering of ethylene production by the plant tissue. Therefore, one is enabled to employ less 2-chloroethylphosphonic acid, thereby avoiding undesirable side effects, or one may achieve greater growth regulating effects at the same 2-chloroethylphosphonic acid concentration. Further, since the compounds added to the phosphonic acid are fungicides, postharvest disease control is possible.

DESCRIPTION OF THE PREFERRED EMBODIMENTS

The use of 2-chloroethylphosphonic acid in plant growth regulation is described in U.S. Pat. No. 3,879,188. At least 15 different responses are attributed to the internal plant tissue ethylene release induced by the compound. These include: (1) increased yields, (2) auxin activity, (3) inhibition of terminal growth, control of apical dominance, increased branching and tillering, (4) altered biochemical composition of the plant, (5) abscission of folliage, flowers, and fruit, (6) hastened ripening and color promotion in fruit, (7) increased flowering and fruiting, (8) abortion or inhibition of flowering and seed development, (9) prevention of lodging, (10) stimulation of seed germination and breaking of dormancy, (11) resistance to freeze injury, (12) hormone or epinasty effects, (13) interaction with other growth regulators, (14) interaction with herbicides, and (15) disease resistance. 2-Chloroethylphosphonic acid or precursors or derivatives thereof are demonstrated in the course of 128 specific examples of the patent to achieve one or more of these ethylene-induced responses in a wide variety of plants, seeds, fruits, and vegetables. The use of concentrations within a range of from 10 to 48000 ppm or 0.1 to 16 kg/hectare is advocated.

According to the present invention, this ethylene release and the responses it induces are enhanced by the addition to 2-chloroethylphosphonic acid or a precursor thereof, of a compound selected from the group:

N-[(trichloromethyl)thio] phthalimide:

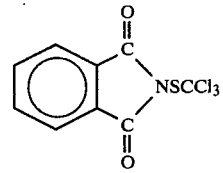

cis-N-[(trichloromethyl)thio]-4-cyclohexene-1,2-dicarboximide:

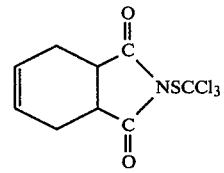

cis-N-[(1,1,2,2-tetrachloroethyl)thio]-4-cyclohexene-1,2-dicarboximide:

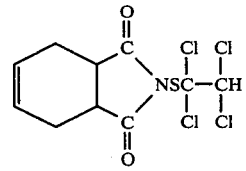

ferric dimethyldithiocarbamate:

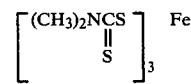

ethylenebisdithiocarbamate manganese:

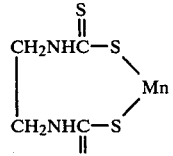

ethylenebisdithiocarbamate zinc:

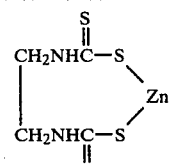

methyl-1-(butylcarbamoyl)-2-benzimidazolecarbamate:

-continued

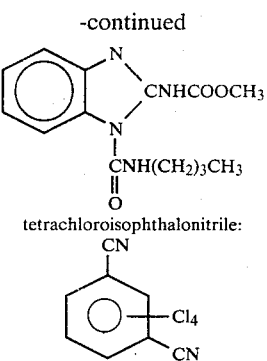

tetrachloroisophthalonitrile:

CN
⟨⟩—Cl₄
CN

In each instance, although the compound itself does not significantly increase internal plant tissue ethylene production, the quantity of ethylene which 2-chloroethylphosphonic acid causes to be released in the plant tissue is greatly increased. Thus, where previously from 50–5000 ppm of 2-chloroethylphosphonic acid alone would be employed, it is now possible, by the addition of from 25 to 10000 ppm of the additive compound, to reduce the amount of 2-chloroethylphosphonic acid to within a range of from 25 to 2500 ppm. Expressed in another fashion, from 0.25 to 5 kg/hectare of 2-chloroethylphosphonic acid is employed together with from 0.25 to 10 kg/hectare of the additive compound. Such amounts in general constitute a "growth regulating amount" of the mixture. Typically the components are present in a ratio of from 0.1 to 50 parts by weight of the additive compound per part of 2-chloroethylphosphonic acid, preferably 0.2 to 4:1, and especially 0.5 to 2:1 parts.

The composition will generally be applied as an aqueous spray, this being most convenient and economical, although dusting or other methods of application are possible. Preparation of the aqueous formulation merely requires the dispersion of the materials at the stated concentration ranges, generally employing a non-phytotoxic surfactant, such as polyoxyethylated sorbitan monolaurate.

The time of application of the active ingredient-containing formulation is generally dependent upon the growth regulating effect desired, for example, before harvesting in the event that fruit abscission is the desired result, before marketing if fruit ripening is desired, etc. Usually it is found that the combination of ingredients, probably because of the higher ethylene levels realized, achieves the desired effect 1 to 2 days earlier than with the use of 2-chloroethylphosphonic acid alone. Application itself may be by any convenient method, typically by a low volume spray application or to run-off.

In order that those skilled in the art may more readily understand the present invention and certain preferred embodiments by which it may be carried into effect, the following specific examples are afforded.

EXAMPLE 1

Aqueous formulations having the concentrations and compositions indicated in Table I are prepared. While the formulation in question is being stirred, sweet cherries (Bing) with stems are immersed therein for five seconds, removed and allowed to dry. The dried cherries are placed in 125 ml Erlenmeyer flasks and incubated at 24° C. daytime (12 hours), 16° C. nighttime, 60% relative humidity, and under a (day) light intensity of 3000 foot candles. At the indicated intervals, the flasks are capped for 2 hours following which a gas phase sample is taken and analyzed on a gas chromatograph sensitive to 10 ppb. Each result is the average of 3 tests, 5 cherries per test.

TABLE I

| CEPA[1] (ppm) | Compound | (ppm) | $C_2H_4$ ($\mu$l/kg fw/hr)[2] 1 day | 2 days | 3 days | Ratio Actual: Additive $C_2H_4$ |
|---|---|---|---|---|---|---|
| — | — | — | 0.07 | 0.07 | 0.07 | — |
| 250 | — | — | 3.25 | 2.07 | 1.26 | — |
| — | tetrachloroisophthalonitrile | 500 | 0.10 | 0.11 | 0.09 | — |
| 250 | " | 500 | 4.84 | 2.92 | 1.26 | 1.37 |
| — | N-[(trichloromethyl)thio] phthalimide | 500 | 0.14 | 0.11 | 0.15 | — |
| 250 | " | 500 | 4.44 | 2.77 | 1.66 | 1.32 |
| — | cis-N-[(trichloromethyl)thio]-4-cyclohexene-1,2-dicarboximide | 500 | 0.13 | 0.15 | 0.13 | — |
| 250 | | 500 | 4.25 | 3.48 | 0.96 | 1.32 |
| — | cis-N-[(1,1,2,2-tetrachloroethyl)thio]-4-cyclohexene-1,2-dicarboximide | 500 | 0.15 | 0.11 | 0.15 | — |
| 250 | | 500 | 5.32 | 2.92 | 1.92 | 1.51 |
| — | ferric dimethyldithiocarbamate | 500 | 0.10 | 0.15 | 0.15 | — |
| 250 | " | 500 | 4.14 | 2.48 | 1.18 | 1.20 |
| — | ethylenebisdithiocarbamate Mn | 500 | 0.10 | 0.10 | 0.20 | — |
| 250 | " | 500 | 4.03 | 2.63 | — | 1.27 |
| — | ethylenebisdithiocarbamate Zn | 500 | 0.17 | 0.17 | 0.15 | — |
| 250 | " | 500 | 4.03 | 2.55 | 1.74 | 1.22 |
| — | methyl-1-(butylcarbamoyl)-2-benzimidazolecarbamate | 500 | 0.13 | 0.15 | 0.15 | — |
| 250 | | 500 | 6.47 | 3.95 | 2.18 | 1.88 |

[1]2-chloroethylphosphonic acid
[2]microliters/kilogram of fruit weight/hour

From the table, the ability of the various compounds to increase the amount of ethylene release triggered by 2-chloroethylphosphonic acid is apparent, despite the fact that the additives alone are without significant effect.

EXAMPLE 2

The procedure of Example 1 is repeated using 250 ppm of CEPA and quantities of tetrachloroisophthalonitrile sufficient to achieve ratios of 1:1, 1:2, and 1:4. After 2 days, the ratio of $C_2H_4$ measured to that expected by the additive effect of the compounds alone is, respectively, 1.68, 1.79, and 1.55.

The same test on another day yields values of 1.43, 1.43, and 1.27, respectively.

EXAMPLE 3

Aqueous formulations of 2-chloroethylphosphonic acid (CEPA) and/or tetrachloroisophthalonitrile (TCIPN) are prepared at the concentrations shown in Table II. Each of the formulations is applied by spraying to 2 entire apple trees, 3 gallons per tree. At the indicated intervals 10 apples are harvested from each tree, measuring the pull force required to separate the fruit from the stem (as described by L. J. Edgerton, Hort Science, Vol. 6, No. 4, Aug. 1971). The apples are then placed in a sealed 10 liter container for 1 hour prior to taking a gas sample for ethylene analysis as in Example 1. Next, the fruit firmness is measured on an Effegi fruit tester. Finally, the color of the Rome apples (at 7 days) and the McIntosh (at 11 days) is determined to ascertain the degree of redness.

TABLE II

| Treatment | | Time After Treatment | Ethylene (μl/kg fw/hr) | Pull Force (kg) | Firmness (kg) | Fruit[3] Drop | Color % |
|---|---|---|---|---|---|---|---|
| Active Ingredient | Concentration (ppm) | | | | | | |
| None | 0 | 4 days[1] | 0.1 | 2.8 | — | — | 60 |
| CEPA | 250 | " | 0.9 | 2.2 | — | — | 80 |
| TCIPN | 500 | " | 0.1 | 2.6 | — | — | 60 |
| CEPA + TCIPN | 250 + 500 | " | 1.6 | 1.7 | — | — | 95 |
| None | 0 | 7 days[2] | 0.1 | 1.1 | 4.2 | 2 | 60 |
| CEPA | 250 | " | 119.6 | 0.6 | 3.5 | 30 | 80 |
| " | 500 | " | 138.8 | 0.2 | 3.5 | 55 | 95 |
| TCIPN | 500 | " | 0.3 | 1.1 | 4.1 | 3 | 60 |
| CEPA + TCIPN | 250 + 500 | " | 170.6 | 0.4 | 3.1 | 50 | 94 |
| CEPA + TCIPN | 500 + 500 | " | 159.0 | 0.1 | 3.2 | 83 | 97 |

[1]variety Red Rome
[2]variety McIntosh
[3]fruit drop = % of crop on ground

Synergistic ethylene release is noted as in Example 1. Further, the known correlation between ethylene release and growth modification effects (e.g., abscission, firmness, and color) is confirmed.

EXAMPLE 4

Mature green Campbell 1327 tomatoes are harvested, washed, sorted, and dried prior to dipping in aqueous solutions of the concentrations listed below. The tomatoes are then air dried, loosely covered, and incubated under the conditions of Example 1. Measurements are made 8 days later with the results set forth indicating an average of 5 fruits each.

TABLE III

| CEPA (ppm) | TCIPN (ppm) | $C_2H_4$ (ppm/ml) | Ripeness (% red color) |
|---|---|---|---|
| 0 | 0 | 1.69 | 27 |
| 0 | 100 | 1.80 | 34 |
| 0 | 250 | 0.85 | 6 |
| 0 | 500 | 0.19 | 2 |
| 0 | 1000 | 0.11 | 0 |
| 500 | 0 | 2.09 | 40 |
| 500 | 100 | 4.19 | 54 |
| 500 | 250 | 4.88 | 76 |
| 500 | 500 | 5.74 | 76 |

In discussing the invention and in the claims, reference is made to the effect of the additive compounds, on 2-chloroethylphosphonic acid. It should be recognized, however, that the enhancement of the ethylene-releasing effect is independent of the source of the 2-chloroethylphosphonic acid. Thus, the compound per se may be employed from the start or precursors thereof, such as the monoester, which degrade in situ to 2-chloroethylphosphonic acid, may be employed.

We claim:

1. A composition for synergistically enhancing the ethylene release promoting effect of 2-chloroethylphosphonic acid in plant tissue consisting essentially of an ethylene release promoting amount of 2-chloroethylphosphonic acid and tetrachloroisophthalonitrile wherein the ratio of tetrachloroisophthalonitrile to 2-chloroethylphosphonic acid is within the range of from about 0.2 to 4:1 parts by weight.

2. A composition as in claim 1 wherein the ratio of tetrachloroisophthalonitrile to 2-chloroethylphosphonic acid is within the range of from 0.5 to 2:1 parts by weight.

3. A method of synergistically enhancing the ability of 2-chloroethylphosphonic acid to release ethylene in plant tissue, which method comprises providing a mixture of tetrachloroisophthalonitrile and 2-chloroethylphosphonic acid in a ratio of from about 0.2 to 4:1 parts by weight and applying a growth-regulating amount of said mixture to a plant.

4. A method as in claim 3 wherein the ratio is 0.5 to 2:1.

5. A method as in claim 3 wherein said growth-regulating amount of said mixture comprises from 0.25 to 2.0 kg/hectare of 2-chloroethylphosphonic acid and 0.25 to 4.0 kg/hectare of tetrachloroisophthalonitrile.

* * * * *